United States Patent
Chen et al.

(10) Patent No.: US 11,414,698 B2
(45) Date of Patent: Aug. 16, 2022

(54) METHOD OF QUANTIFYING MUTANT ALLELE BURDEN OF TARGET GENE

(71) Applicant: CHANG GUNG MEDICAL FOUNDATION CHANG GUNG MEMORIAL HOSPITAL AT CHIAYI, Chiayi (TW)

(72) Inventors: Chih-Cheng Chen, Chiayi (TW); Chia-Chen Hsu, Chiayi (TW)

(73) Assignee: CHANG GUNG MEDICAL FOUNDATION CHANG GUNG MEMORIAL HOSPITAL AT CHIAYI, Chiayi (TW)

(*) Notice: Subject to any disclaimer, the term of this patent is extended or adjusted under 35 U.S.C. 154(b) by 348 days.

(21) Appl. No.: 16/357,706

(22) Filed: Mar. 19, 2019

(65) Prior Publication Data

US 2019/0292586 A1  Sep. 26, 2019

Related U.S. Application Data

(60) Provisional application No. 62/646,646, filed on Mar. 22, 2018.

(51) Int. Cl.
| | |
|---|---|
| *C12Q 1/68* | (2018.01) |
| *C12Q 1/6851* | (2018.01) |
| *C12Q 1/686* | (2018.01) |
| *C12Q 1/6827* | (2018.01) |
| *C12Q 1/6876* | (2018.01) |

(52) U.S. Cl.
CPC .......... *C12Q 1/6851* (2013.01); *C12Q 1/686* (2013.01); *C12Q 1/6827* (2013.01); *C12Q 1/6876* (2013.01); *C12Q 2600/156* (2013.01); *C12Q 2600/16* (2013.01); *C12Q 2600/166* (2013.01)

(58) Field of Classification Search
CPC ........................................ C12Q 1/68
USPC ........................................ 435/6.12
See application file for complete search history.

(56) References Cited

PUBLICATIONS

Fantasia et al., A highly specific q-RT-PCR assay to address the relevance of the JAK2WT and JAK2V617F expression levels and control genes in Ph-negative myeloproliferatve neoplasms, Ann Hematol. Apr. 2014;93(4):609-16. doi: 10.1007/s00277-013-1920-0. Epub Oct. 31, 2013.*

White et al., A certified plasmid reference material for the standardisation of BCR-ABL1 mRNA quantification by real-time quantitative PCR, Leukemia. Feb. 2015;29(2):369-76. doi: 10.1038/leu.2014.217. Epub Jul. 18, 2014.*

(Continued)

*Primary Examiner* — Aaron A Priest
(74) *Attorney, Agent, or Firm* — Nixon & Vanderhye PC

(57) ABSTRACT

Disclosed herein is a method of quantifying a mutant allele burden of a target gene in a subject. The method includes providing a first plasmid that includes a mutant allele sequence and an internal control sequence, and a second plasmid that includes a wild-type allele sequence and the internal control sequence, and subjecting DNA of the subject to quantitative polymerase chain reaction to measure a mutant allele expression level of the target gene, so as to determine the mutant allele burden of the target gene in the subject based on a standard curve of the mutant allele burden of the target gene created by serial dilution of the first and second plasmids.

10 Claims, 8 Drawing Sheets

Specification includes a Sequence Listing.

(56) References Cited

PUBLICATIONS

Beillard et al., Evaluation or candidate control genes for diagnosis and residual disease detection in leukemic patients using 'real-time' quantitative reverse-transcriptase polymerase chain reaction (RQ-PCR)—a Europe against cancer program, Leukemia. Dec. 2003;17(12):2474-86. doi: 10.1038/sj.leu.2403136.*

Zapparoli et al., Quantitative threefold allele-specific PCR (QuanTAS-PCR) for highly sensitive JAK2V617F mutant allele detection, BMC Cancer 13, 206 (2013). https://doi.org/10.1186/1471-2407-13-206.*

Szankasi et al., A quantitative allele-specific PCR test for the BRAF V600E mutation using a single heterozygous control plasmid for quantitation: a model for qPCR testing without standard curves, J Mol Diagn. Mar. 2013;15(2):248-54. doi: 10.1016/j.jmoldx.2012.11.005. Epub Jan. 8, 2013.*

* cited by examiner

SEQUENCE LISTING

<160> NUMBER OF SEQ ID NOS: 17

<210> SEQ ID NO 1
<211> LENGTH: 28
<212> TYPE: DNA
<213> ORGANISM: Artificial Sequence
<220> FEATURE:
<223> OTHER INFORMATION: Forward primer H_JAK2_clon_exon21_F

<400> SEQUENCE: 1
cagtataata tggcagagta aaacaata                                28

<210> SEQ ID NO 2
<211> LENGTH: 30
<212> TYPE: DNA
<213> ORGANISM: Artificial Sequence
<220> FEATURE:
<223> OTHER INFORMATION: Reverse primer H_JAK2_clon_exon21_R

<400> SEQUENCE: 2
cctttattat ctatgaaaac gtctagatga                              30

<210> SEQ ID NO 3
<211> LENGTH: 264
<212> TYPE: DNA
<213> ORGANISM: Homo sapiens

<400> SEQUENCE: 3
ggtatgaccc tctacaggac aacactgggg aggtggtcgc tgtaaaaaag cttcagcata    60
gtactgaaga gcacctaaga gactttgaaa gggaaattga atcctgaaa tccctacagc   120 atgacaacat tgtaaagtac aagggagtgt gctacagtgc tggtaagctg cccattgaaa   180
cctattttaa attcaaggta tgtgtttggc atcctgtgta atataaatgt acaatgtctt   240
aacgatctgg acttatgcca atgc                                          264

<210> SEQ ID NO 4
<211> LENGTH: 36
<212> TYPE: DNA
<213> ORGANISM: Artificial Sequence
<220> FEATURE:
<223> OTHER INFORMATION: Forward primer BamHI-hJAK2_WT/V617F_F

<400> SEQUENCE: 4
gatatggatc cggaccaaag cacattgtat cctcat                       36

<210> SEQ ID NO 5
<211> LENGTH: 34
<212> TYPE: DNA
<213> ORGANISM: Artificial Sequence
<220> FEATURE:
<223> OTHER INFORMATION: Reverse primer SalI-hJAK2_WT/V617F_R

<400> SEQUENCE: 5
atatagtcga cgtcgacctg acacctagct gtga                         34

<210> SEQ ID NO 6
<211> LENGTH: 323
<212> TYPE: DNA
<213> ORGANISM: Homo sapiens

<400> SEQUENCE: 6
ggaccaaagc acattgtatc ctcatctata gtcatgctga agtaggaga aagtgcatct    60 ttattatggc agagagaatt ttctgaacta tttatggaca acagtcaaac aacaattctt   120

```
tgtactttt tttttcctta gtctttcttt gaagcagcaa gtatgatgag caagctttct    180
cacaagcatt tggttttaaa ttatggagta tgtgtctgtg gagacgagag taagtaaaac    240
tacaggcttt ctaatgcctt tctcagagca tctgttttttg tttatataga aaattcagtt    300
tcaggatcac agctaggtgt cag                                            323
```

<210> SEQ ID NO 7
<211> LENGTH: 323
<212> TYPE: DNA
<213> ORGANISM: Homo sapiens

<400> SEQUENCE: 7

```
ggaccaaagc acattgtatc ctcatctata gtcatgctga aagtaggaga aagtgcatct    60
ttattatggc agagagaatt ttctgaacta tttatggaca acagtcaaac aacaattctt    120 tgtactttt tttttcctta gtctttcttt gaagcagcaa gtatgatgag caagctttct    180
cacaagcatt tggttttaaa ttatggagta tgtttctgtg gagacgagag taagtaaaac    240
tacaggcttt ctaatgcctt tctcagagca tctgttttttg tttatataga aaattcagtt    300
tcaggatcac agctaggtgt cag                                            323
```

<210> SEQ ID NO 8
<211> LENGTH: 27
<212> TYPE: DNA
<213> ORGANISM: Artificial Sequence
<220> FEATURE:
<223> OTHER INFORMATION: Forward primer H_JAK2_V617_F

<400> SEQUENCE: 8

```
ttatggacaa cagtcaaaca acaattc                                        27
```

<210> SEQ ID NO 9
<211> LENGTH: 21
<212> TYPE: DNA
<213> ORGANISM: Artificial Sequence
<220> FEATURE:
<223> OTHER INFORMATION: Reverse primer H_JAK2_V617_R

<400> SEQUENCE: 9

```
cttactctcg tctccacaaa a                                              21
```

<210> SEQ ID NO 10
<211> LENGTH: 40
<212> TYPE: DNA
<213> ORGANISM: Artificial Sequence
<220> FEATURE:
<223> OTHER INFORMATION: H_JAK2_probe_FAM
<220> FEATURE:
<221> NAME/KEY: misc_feature
<223> OTHER INFORMATION: labeled with fluorescein at the 5'-end
<220> FEATURE:
<221> NAME/KEY: misc_feature
<223> OTHER INFORMATION: labeled with Iowa Black FQ (IABkFQ) at the
      3'-end

<400> SEQUENCE: 10

```
ttgtactttt tttttccctt agtctttctt tgaagcagca                          40
```

<210> SEQ ID NO 11
<211> LENGTH: 32
<212> TYPE: DNA
<213> ORGANISM: Artificial Sequence
<220> FEATURE:
<223> OTHER INFORMATION: Forward primer H_JAK2_ref_ex21_F

<400> SEQUENCE: 11
ggaatattta ccatatggaa gtttacgaga ct                                32

<210> SEQ ID NO 12
<211> LENGTH: 25
<212> TYPE: DNA
<213> ORGANISM: Artificial Sequence
<220> FEATURE:
<223> OTHER INFORMATION: Reverse primer H_JAK2_ref_ex21_R

<400> SEQUENCE: 12
caacacggtt gcttcatcta cagca                                        25

<210> SEQ ID NO 13
<211> LENGTH: 34
<212> TYPE: DNA
<213> ORGANISM: Artificial Sequence
<220> FEATURE:
<223> OTHER INFORMATION: H_JAK2_ref_probe_HEX
<220> FEATURE:
<221> NAME/KEY: misc_feature
<223> OTHER INFORMATION: labeled with hexachloro-fluorescein at the
      5'-end
<220> FEATURE:
<221> NAME/KEY: misc_feature
<223> OTHER INFORMATION: labeled with Iowa Black FQ (IABkFQ) at the
      3'-end

<400> SEQUENCE: 13
acggatagat cacataaaac ttctgcagta caca                              34

<210> SEQ ID NO 14
<211> LENGTH: 22
<212> TYPE: DNA
<213> ORGANISM: Artificial Sequence
<220> FEATURE:
<223> OTHER INFORMATION: H_JAK2_WT_blocker
<220> FEATURE:
<221> NAME/KEY: misc_feature
<223> OTHER INFORMATION: labeled with di-deoxycytidine at the 5'-end

<400> SEQUENCE: 14
tacttactct cgtctccaca aa                                           22

<210> SEQ ID NO 15
<211> LENGTH: 25
<212> TYPE: DNA
<213> ORGANISM: Artificial Sequence
<220> FEATURE:
<223> OTHER INFORMATION: Forward primer H_HCK_F

<400> SEQUENCE: 15
tattagcacc atccatagga ggctt                                        25

<210> SEQ ID NO 16
<211> LENGTH: 22
<212> TYPE: DNA
<213> ORGANISM: Artificial Sequence
<220> FEATURE:
<223> OTHER INFORMATION: Reverse primer H_HCK_R

<400> SEQUENCE: 16
gttagggaaa gtggagcgga ag                                           22

<210> SEQ ID NO 17
<211> LENGTH: 24

```
<212> TYPE: DNA
<213> ORGANISM: Artificial Sequence
<220> FEATURE:
<223> OTHER INFORMATION: H_HCK_probe_HEX
<220> FEATURE:
<221> NAME/KEY: misc_feature
<223> OTHER INFORMATION: labeled with hexachloro-fluorescein at the
      5'-end
<220> FEATURE:
<221> NAME/KEY: misc_feature
<223> OTHER INFORMATION: labeled with Iowa Black FQ (IABkFQ) at the
      3'-end

<400> SEQUENCE: 17
taacgcgtcc accaaggatg cgaa                                            24
```

METHOD OF QUANTIFYING MUTANT ALLELE BURDEN OF TARGET GENE

CROSS-REFERENCE TO RELATED APPLICATION

This application claims priority of U.S. Provisional Patent Application No. 62/646,646, filed on Mar. 22, 2018.

SEQUENCE LISTING

The instant application contains a Sequence Listing which has been filed electronically in ASCII format.

FIELD

The disclosure relates to a method of quantifying a mutant allele burden of a target gene by using a recombinant plasmid pair as a standard.

BACKGROUND

Classical myeloproliferative neoplasms (MPNs) are multipotent hematopoietic stem cell disorders characterized by excess production of various blood cells. MPNs include three major clinical entities, i.e., polycythemia vera (PV), essential thrombocythemia (ET) and primary myelofibrosis (PMF). A hallmark of the genetic background of MPNs that constitutes the diagnostic criteria of World Health Organization (WHO) classification is MPN-restricted driver mutations, including those in Janus kinase 2 (JAK2), calreticulin (CALR) and myeloproliferative leukemia virus (MPL). Mutations in any one of the mutually exclusive driver genes result in constitutive activation of downstream signaling cascades, which in turn leads to clonal proliferation of hematopoietic precursors and excessive production of terminally differentiated, fully functional blood cells.

In regard to classical MPNs, mutations in JAK2 include JAK2 V617F hotspot mutation and exon 12 mutations. In particular, allele burden of JAK2 V617F carries important pathogenetic and clinical significances in MPNs. Previous studies have demonstrated that JAK2 V617F homozygosity could drive phenotypic switch from ET to PV in mice models, and the higher allele burden in PV than in ET as seen in clinical studies is associated with unique disease phenotypes even within a specific MPN subtype. For example, MPN patients with higher allele burden of JAK2 V617F are more likely to suffer from major thrombotic events. These studies highlight the importance of precise determination and quantification of JAK2 V617F mutant allele burden in afflicted individuals.

A large number of diagnostic techniques have been applied in the detection of JAK2 V617F mutation in MPNs, including direct sequencing, pyrosequencing, denaturing high performance liquid chromatography, restriction enzyme digestion, melting curve analysis, amplification-refractory mutation system, and allele-specific polymerase chain reaction (AS-PCR). Among these diagnostic techniques, AS-PCR seems to be the most commonly used method and allows detection of an allele burden as low as 1%; however, the obtained results are usually ambiguous. There have been great efforts to improve the accuracy of detecting and quantifying JAK2 V617F mutation, such as allele-specific loop-mediated isothermal amplification, addition of a wild-type JAK2 blocker (any one of a non-extendible dideoxy oligonucleotide, a locked nucleic acid, and a peptide nucleic acid) to limit amplification to be mutant-specific in a quantitative PCR (q-PCR) reaction, and restriction fragment nested AS-PCR. Unfortunately, a multicenter study reported existence of significant discrepancies in the results of JAK2 V617F mutant allele burden quantitation when blinded samples were tested across some of the most specialized health institutes, which delineated the importance of using well-defined, accurate standards to refine JAK2 quantitative assays. Although DNA from JAK2-mutated UKE-1 and HEL cells are commonly used for creation of standard curves in quantification of JAK2 V617F mutation, neither cells are considered ideal, as HEL cells carry multiple copies of JAK2, and UKE-1 cells do undergo clonal evolution with increasing JAK2 copies during in vitro cultures, which might lead to an underestimation of the JAK2 V617F mutant allele burden.

Therefore, there is still an increasing need for precise quantification and increased sensitivity detection of low JAK2 V617F mutant allele burden.

SUMMARY

Therefore, an object of the present disclosure is to provide a method of quantifying a mutant allele burden of a target gene that can alleviate at least one of the drawbacks associated with the prior art.

According to the present disclosure, the method of quantifying a mutant allele burden of a target gene in a subject includes:
providing a first plasmid that includes a mutant allele sequence located at a first region of the target gene, and an internal control sequence derived from the target gene and located at a second region of the target gene, the second region being different from the first region;
providing a second plasmid that includes a wild-type allele sequence located at the first region of the target gene, and the internal control sequence;
subjecting genomic DNA of the subject to a first quantitative polymerase chain reaction (q-PCR) using a reaction mixture containing a mutant allele-specific primer pair and a first detectable probe for detecting the mutant allele sequence, and an internal control sequence-specific primer pair and a second detectable probe for detecting the internal control sequence, so as to measure a mutant allele expression level of the target gene;
subjecting standard diluents of the first plasmid formed from serial dilution with the second plasmid to a second q-PCR using the reaction mixture, so as to create a standard curve of the mutant allele burden of the target gene; and
correlating the measured mutant allele expression level of the target gene to the standard curve, so as to determine the mutant allele burden of the target gene in the subject.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
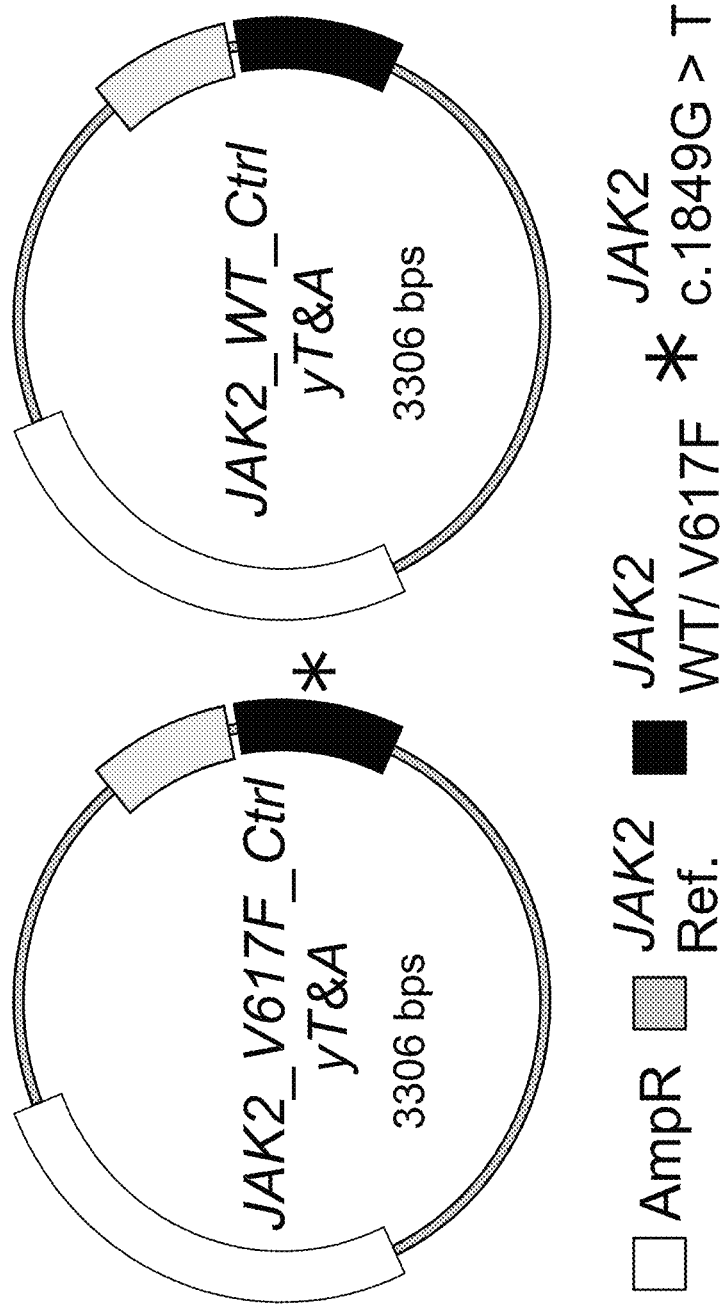
FIG. 1 shows the constructs of recombinant plasmids JAK2_WT_Ctrl_yT&A and JAK2_V617F_Ctrl_yT&A, in which AmpR represents an ampicillin resistance gene, JAK2 Ref. represents partial JAK2 exon 21 as an internal control, JAK2 WT/V617F represents wild-type or mutant JAK2 exon 14, and JAK2 c.1849 G>T represents JAK2 V617F mutation position.

It is to be understood that, if any prior art publication is referred to herein, such reference does not constitute an admission that the publication forms apart of the common general knowledge in the art, in Taiwan or any other country.

For the purpose of this specification, it should be clearly understood that the word "comprising" means "including but not limited to", and that the word "comprise" has a corresponding meaning.

Unless otherwise defined, all technical and scientific terms used herein have the meaning as commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described. For clarity, the following definitions are used herein.

The terms "nucleic acid", "nucleic acid sequence", and "nucleic acid fragment" as used herein refer to a deoxyribonucleotide or ribonucleotide sequence in single-stranded or double-stranded form, and comprise naturally occurring nucleotides or artificial chemical mimics. The term "nucleic acid" as used herein is interchangeable with the terms "gene", "cDNA", "mRNA", "oligo-nucleotide", and "polynucleotide" in use.

Unless otherwise indicated, a nucleic acid sequence, in addition to the specific sequences described herein, also covers its complementary sequence, and the conservative analogs, related naturally occurring structural variants and/or synthetic non-naturally occurring analogs thereof, for example, homologous sequences having degenerate codon substitution, and conservative deletion, insertion, substitution, or addition. Specifically, degenerative codon substitution may be produced by, for instance, a nucleotide residue substitution at the third position of one or more selected codons in a nucleic acid sequence with other nucleotide residue(s).

As used herein, the term "allele" refers generally to alternative DNA sequences at the same physical locus on a segment of DNA, such as, for example, on homologous chromosomes. An allele can refer to DNA sequences which differ between the same physical locus found on homologous chromosomes within a single cell or organism or which differ at the same physical locus in multiple cells or organisms ("allelic variant"). In certain embodiments, an allele can correspond to a single nucleotide difference at a particular physical locus. In other embodiments, an allele can correspond to nucleotide (single or multiple) insertion or deletion.

The term "wild-type" as used herein refers to a gene or allele which has the characteristics of that gene or allele when isolated from a naturally occurring source. A wild-type gene or a wild-type allele is that which is most frequently observed in a population and is arbitrarily designated as the "normal" or "wild-type" form of the gene or allele.

As used herein, the term "mutant" or "mutated" refers to a gene or allele which displays modifications in sequence when compared to the wild-type gene or allele. The term "mutation" refers to a change in the sequence of nucleotides of a normally conserved nucleic acid sequence resulting in the formation of a mutants differentiated from the normal (unaltered) or wild type sequence. Mutations can generally be divided into two general classes, namely, base-pair substitutions (e.g. single nucleotide substitutions) and frameshift mutations. The latter entail the insertion or deletion of one to several nucleotide pairs.

As used herein, the term "allele burden" or "mutant allele burden" refers to the ratio of mutant allele to the total allele (i.e. the combination of the mutant and wild-type alleles) in, for example, hematopoietic cells.

The term "primer" as used herein refers to a single-stranded oligonucleotide capable of acting as a point of initiation of template-directed DNA synthesis under appropriate conditions, in an appropriate buffer and at a suitable temperature. The appropriate length of a primer depends on the intended use of the primer, but typically ranges from 15 to 30 nucleotides. A primer sequence need not be exactly complementary to a template, but must be sufficiently complementary to hybridize with a template.

As used herein, the term "primer pair" means a set of primers including a 5' upstream primer, which hybridizes to the 5' end of the DNA sequence to be amplified and a 3' downstream primer, which hybridizes to the complement of the 3' end of the sequence to be amplified.

The term "allele-specific primer" as used herein refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient, inefficient or undetectable.

As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

As used herein, the term "target gene", "target sequence", "target nucleic acid" or "target DNA" refers to a portion of the nucleic acid sequence which is to be either amplified, detected or both.

The terms "patient", "subject" and "individual" are used interchangeably herein, and mean a mammalian (e.g., human) subject to be treated and/or to obtain a biological sample therefrom.

As used herein, the term "sample" or "clinical sample" refers to any composition containing or presumed to contain nucleic acid. This includes a sample of tissue or fluid isolated from an individual, for example, skin, plasma, serum, spinal fluid, lymph fluid, synovial fluid, urine, tears, blood cells, organs and tumors, and also samples of in vitro cultures established from cells taken from an individual, including the formalin-fixed paraffin embedded tissues (FF-PET) and nucleic acids isolated therefrom.

The term "quantitative PCR" or simply "q-PCR" as used herein is given the definition of a laboratory technique based on polymerase chain reaction (PCR), which is used to amplify and simultaneously detect or quantify a targeted nucleic acid molecule (e.g., a DNA molecule). In contrast to standard PCR where the reaction product is detected after amplification has ended, the key feature of q-PCR is that the nucleic acid molecule (e.g. DNA molecule or DNA fragment) is being detected during amplification as the reaction progresses in "real time", and hence, the alternative name of q-PCR is "real-time PCR". An amplified DNA molecule is detected in real time either by intercalation of non-specific fluorescent dyes with any double-stranded DNA, or sequence-specific DNA probes having oligonucleotides that are labelled with a fluorescent reporter (e.g., fluorescein-based dyes such as FAM, HEX, 2'-chloro-7'phenyl-1,4-dichloro-6-carboxy-fluorescein (VIC), tetrachlorofluorescein (TET), and 6-carboxy-4',5'-dichloro-2',7'-dimethoxyfluorescein (JOE), and rhodamine-based dyes such as 6-carboxy-X-rhodamine (ROX), tetramethylrhodamine (TAMRA) and sulforhodamine 101 acid chloride (Texas Red)) which permits detection only after hybridization of the probe with its complementary target sequence. It is known that when two DNA probes for detecting different DNA molecules are simultaneously used in a q-PCR assay, the fluorescent reporter labeled on the DNA probes should be different from one another. The fluorescent signals generated during amplification are detected by an appropriate optical detection system and are tracked from the moment the signals pass the background threshold till the reaction reaches plateau. The copy number of the target sequences can be estimated using either relative or absolute quantification strategy, typically by analyzing the shape of the obtained amplification curve (also known as a standard curve), or by determining when the fluorescent signals rises above a cycle threshold value (often called $C_t$ value). In relative quantification strategy, the target nucleic acid levels estimated in a given sample using the $C_t$ or standard curve analysis are expressed as relative to values obtained for the same target in another reference sample, for example, an untreated control sample. Conversely, in absolute quantification strategy, the q-PCR signal is related to input copy number using a standard curve, or can be calculated according to a digital PCR method. These and other q-PCR quantification strategies are well known to those skilled in the art and their calculation can differ depending on a given application and a q-PCR system.

As used herein, the term "$C_t$" or "$C_t$ value" refers to cycle threshold and signifies the cycle of a q-PCR amplification assay in which fluorescent signal from a reporter or probe that is indicative of amplicon generation first becomes detectable above a background level. In certain embodiments, the $C_t$ is the cycle number at which the q-PCR amplification becomes exponential. In certain embodiments, the greater the quantity of target DNA in the starting material, the faster a significant increase in fluorescent signal will appear, yielding a lower $C_t$.

As used herein, the term "$\Delta C_t$", "delta $C_t$" or "$dC_t$" refers to the difference in the numerical cycle number of PCR at which the signal passes the fixed threshold between two different samples or reactions. In certain embodiments, $\Delta C_t$ is the difference in numerical cycle number of PCR at which exponential amplification is reached between two different samples or reactions.

According to the present disclosure, a method of quantifying a mutant allele burden of a target gene in a subject includes:

providing a first plasmid that includes a mutant allele sequence located at a first region of the target gene, and an internal control sequence derived from the target gene and located at a second region of the target gene, the second region being different from the first region;

providing a second plasmid that includes a wild-type allele sequence located at the first region of the target gene, and the internal control sequence;

subjecting genomic DNA of the subject to a first quantitative polymerase chain reaction (q-PCR) using a reaction mixture containing a mutant allele-specific primer pair and a first detectable probe for detecting the mutant allele sequence, and an internal control sequence-specific primer pair and a second detectable probe for detecting the internal control sequence, so as to measure a mutant allele expression level of the target gene;

subjecting standard diluents of the first plasmid formed from serial dilution with the second plasmid to a second q-PCR using the reaction mixture, so as to create a standard curve of the mutant allele burden of the target gene; and correlating the measured mutant allele expression level of the target gene to the standard curve, so as to determine the mutant allele burden of the target gene in the subject.

In certain embodiments, the mutant allele sequence has a nucleotide length that is substantially identical to that of the wild-type allele sequence, and the first plasmid has a nucleotide length that is substantially identical to that of the second plasmid.

According to the present disclosure, the reaction mixture for each of the first and second q-PCR may further include a blocking agent that hybridizes to a wild-type allele sequence of the target gene and that inhibits binding of at least one primer of the mutant allele-specific primer pair to the wild-type allele sequence of the target gene.

The term "blocking agent" and "oligonucleotide blocker" are used interchangeably herein, and can be designed to anneal to the same or opposing strand of what the allele-specific primer anneals to and can be modified with a blocking group (e.g., a "non-extendable moiety") at its 3' terminal end, 5' terminal end and/or at an internal position near 3' end within the oligonucleotide blocker. Thus, an oligonucleotide blocker can be designed, for example, so as to tightly bind to a wild type allele (e.g., abundant allelic variant) in order to suppress amplification of the wild type allele while amplification is allowed to occur on the same or opposing strand comprising a mutant allele (e.g., rare allelic variant) by extension of the allele-specific primer. That is, the non-extendable moiety may increase the difference in the Tm between matched and mismatched target sequences and/or decrease mismatch priming efficiency, thereby improving assay specificity and/or selectivity.

In certain embodiments, the blocking agent is an oligonucleotide having a non-extendable moiety at 3'-terminus. Examples of the non-extendable moiety include, but are not limited to peptide nucleic acid (PNA), locked nucleic acid (LNA), zip nucleic acid (ZNA), bridged nucleic acid (BNA), threose nucleic acid (TNA), triazole nucleic acid, amino-C7, non-extendable nucleotide, minor groove binder (MGB), and combinations thereof.

As used herein, the term "non-extendable nucleotide" refers to a nucleotide that blocks nucleic acid polymerization (e.g., blocks polymerase read-through). In some embodiments, the non-extendable nucleotide is a non-naturally occurring nucleotide or a dideoxynucleotide (e.g., 2', 3'-dideoxynucleotides (i.e., di-deoxynucleotide triphosphates (ddNTP), which may include ddGTP, ddATP, ddTTP and ddCTP)). In some embodiments, the non-naturally occurring nucleotide is isoC, isoG, deoxyuridine, 3'-deoxyadenosine, 3'-deoxythymidine, 3'-deoxyguanosine, 3'-deoxycytidine, inverted dT, 5'-methyl-deoxycytidine, 2'-fluoro, 8-aza-7-deaza-dA (ppA), 8-aza-7-deaza-dG (ppG), 2'-deoxypseudoisocytidine (iso dC), 5-fluoro-2'-deoxyuridine (fdU), and/or an otherwise naturally-occurring nucleotide inserted in an inverted orientation.

In an exemplary embodiment, the blocking agent is an oligonucleotide having di-deoxynucleotide triphosphates (ddNTP) at the 3' terminus thereof.

According to the present disclosure, the target gene may have one or more single-nucleotide polymorphisms within the gene. In certain embodiments, the target gene is a disease-associated gene, such as cancer-associated genes and genes associated with a hereditary disease.

Examples of the target gene may include, but are not limited to, JAK2, K-Ras, B-Raf, and EGFR. In an exemplary embodiment, the target gene is JAK2 and the mutant allele sequence is JAK2 V617F.

The present disclosure will be further described by way of the following examples. However, it should be understood that the following examples are intended solely for the purpose of illustration and should not be construed as limiting the disclosure in practice.

EXAMPLES

General Experimental Materials:

1. Primers and probes used in the following examples were synthesized by Integrated DNA Technologies, Inc. (IDT), Iowa, USA.

2. Cell cultures

Human erythroleukemia (HEL) cell line (ATCC TIB-180™) and essential thrombocytopenia (ET)-transformed acute myeloid leukemia (AML) cell line UKE-1 (GM23245) were respectively purchased from American Type Culture Collection (VA, USA) and Coriell Cell Repositories, Coriell Institute for Medical Research (NJ, USA). The cells of the respective type were incubated in a Petri dish containing RPMI-1640 (Gibco) supplemented with 15% FBS and 2 mM L-glutamine, followed by cultivation in an incubator with culture conditions set at 37° C. and 5% $CO_2$. Medium change was performed every 2 days. Cell passage was performed when the cultured cells reached 70% of confluence.

3. Study subjects, blood sample collection and DNA extraction

The following experiments were approved by the Institutional Review Board of Chang-Gung Memorial Hospital, Chiayi, Taiwan. Patients with myeloproliferative neoplasms (MPN), who were followed and treated at Chang-Gung Memorial Hospital, Chiayi, Taiwan, and adult healthy individuals as controls were enrolled as study population. Each participants of this study provided a written informed consent in accordance with the Declaration of Helsinki for blood sample collection.

Peripheral venous blood collected from a respective one of the MPN patients and healthy individuals was placed into an EDTA-containing blood collection tube. Peripheral blood granulocytes were harvested using Ficoll-Hypaque density gradient centrifugation and were cryopreserved in RNAlater™ Stabilization Solution (Cat. No.: AM 7020, Thermo Fisher Scientific). Granulocytic DNA was extracted, and was purified using TRI Reagent® (Cat. No.: T9424, Sigma-Aldrich), followed by dilution with diethylpyrocarbonate (DEPC)-treated $d_2H_2O$, so as to prepare a DNA test sample having a final concentration of 100 ng/μL for further analysis.

General Experimental Procedures:

1. Concerning the experimental methods and relevant techniques for DNA cloning as employed in this disclosure, such as DNA cleavage by restriction enzymes, DNA ligation with T4 DNA ligase, agarose gel electrophoresis, plasmid transformation, etc., reference may be made to the following textbook widely known in the art: Sambrook J. and Russell D. W. (2001), Molecular Cloning: a Laboratory Manual, 3rd ed., Cold Spring Harbor Laboratory Press, New York. The aforesaid techniques can be readily performed by those skilled in the art based on their professional knowledge and experience.

2. Statistical analysis:

The intra- and inter-q-PCR assay variation was obtained by calculating coefficients of variation on allelic burden values using linear regression and/or Pearson's correlation analysis. Each statistical analysis was performed using the Statistical Package for the Social Sciences (SPSS) software version 17.0, purchased from SPSS Inc., Chicago, USA. The level of significance for each statistical analysis was set at 0.05.

Example 1. Construction of Recombinant Plasmids as Standards for Quantifying JAK2 V617F Mutant Allele Burden To minimize copy number variation and to standardize JAK2 V617F allele burden quantification, a pair of recombinant plasmids of this disclosure was constructed as follows.

Since few somatic mutations exist in exon 21 of JAK2 gene, the applicant selected this region as an internal control. Using genomic DNA extracted from HEL cells using TRI Reagent® as a template, a control PCR product (264 bp) having a partial DNA sequence of JAK2 exon 21 was obtained from PCR using a forward primer H_JAK2_clon_exon21_F and a reverse primer H_JAK2_clon_exon21_R as shown in Table 1. The resultant control PCR product was purified and then ligated into a cloning vector using yT&A cloning kit (Yeastern Biotech, Taipei, Taiwan) according to the manufacturer's instructions, so as to obtain a plasmid JAK2_Ctrl_yT&A. According to the sequencing analysis conducted by Sanger sequencing (Manufacturer: ABI; Model: 3730), partial JAK2 exon 21 having a nucleotide sequence as shown in SEQ ID NO: 3 was included in the plasmid JAK2_Ctrl_yT&A.

For detection of JAK2 V617F mutation, exon 14 of JAK2 was selected as a target region. Using a forward primer SalI-hJAK2_WT/V617F_F and a reverse primer BamHI-hJAK2_WT/V617F_R as shown in Table 1, a mutant PCR product (323 bps) having a mutant DNA sequence of JAK2 exon 14 and a wild-type PCR product (323 bps) having a wild-type DNA sequence of JAK2 exon 14 were obtained from PCR respectively using genomic DNA extracted from HEL cells as a mutant DNA template, and DNA extracted from peripheral blood granulocytes of healthy adult individuals as a wild-type DNA template. A respective one of the thus obtained mutant and wild-type PCR products was inserted into the JAK2_Ctrl_yT&A plasmid at the SalI and BamHI sites, so as to generate a corresponding one of a wild-type target recombinant plasmid JAK2_WT_Ctrl_yT&A (3306 bps) and a mutant target recombinant plasmid JAK2_V617F_Ctrl_yT&A (3306 bps) having JAK2 V617F mutation as shown in FIG. 1, in which JAK2 V617F mutation position (cDNA 1849 G>T) is indicated by an asterick. The wild-type and mutant target recombinant plasmids were verified by Sanger sequencing to include partial wild-type JAK2 exon 14 (SEQ ID NO: 6) and partial mutant JAK2 exon 14 (SEQ ID NO: 7), respectively.

TABLE 1

| Target gene region | Primer | Primer's nucleotide sequence (5'→3') | SEQ ID NO. |
|---|---|---|---|
| Exon 21 of Human JAK2 (NCBI accession number: NM_004972.3) | H_JAK2_clon_exon21_F | cagtataatatggcagagtaaaacaata | 1 |
| | H_JAK2_clon_exon21_R | cctttattatctatgaaaacgtctagatga | 2 |
| Exon 14 of Human JAK2 (NCBI accession number: NM_004972.3) | BamHI-hJAK2_WT/V617F_F | gatat<u>ggatcc</u>ggaccaaagcacattgtatcctcat  BamHI | 4 |
| | SalI-hJAK2_WT/V617F_R | atata<u>gtcgac</u>gtcgacctgacacctagctgtga  SalI | 5 |

Note:
The underlined nucleotides each represent the recognition site of a restriction enzyme as indicated below.

Example 2. Validation of the Accuracy of the Recombinant Plasmids of this Disclosure as Standards for Quantifying JAK2 V617F Mutant Allele Burden Experimental Procedures:

The wild-type and mutant target recombinant plasmids JAK2_WT_Ctrl_yT&A and JAK2_V617F_Ctrl_yT&A obtained in Example 1, which respectively represents 0% and 100% JAK2 V617F mutant allele burden, were mixed at various proportions as shown in Table 2 below to obtain six recombinant plasmid mixtures that have a respective JAK2 V617F mutant allele burden (i.e., 100%, 50%, 10%, 1%, 0.1% and 0.01%) for serving as standard diluents for JAK2 V617F mutant allele.

TABLE 2

| JAK2 V617 mutant allele burden (%) | 100 | 50 | 10 | 1 | 0.1 | 0.01 |
|---|---|---|---|---|---|---|
| JAK2_WT_Ctrl_yT&A (μL) | 0 | 50 | 90 | 99 | 99.9 | 99.99 |
| JAK2_V617F_Ctrl_yT&A (μL) | 100 | 50 | 10 | 1 | 0.1 | 0.01 |

The JAK2 V617F mutation in the aforementioned recombinant plasmid mixtures was detected and determined using two commercially available kits, i.e., RGQ PCR kit (Qiagen, Germany) performed on the RGQ PCR system, and PrimePCR™ droplet Digital™ PCR Mutation Detection Assay (ddPCR) kit performed on the QX200™ ddPCR system (Bio-Rad, CA, USA), according to the manufacturer's instructions. The thus calculated JAK2 V617F mutant allele burdens in all of the recombinant plasmid mixtures measured by the Qiagen RGQ PCR kit and the Bio-Rad QX200 ddPCR kit were compared to each other, and then correlated with the expected values using linear regression.

Figure 2:
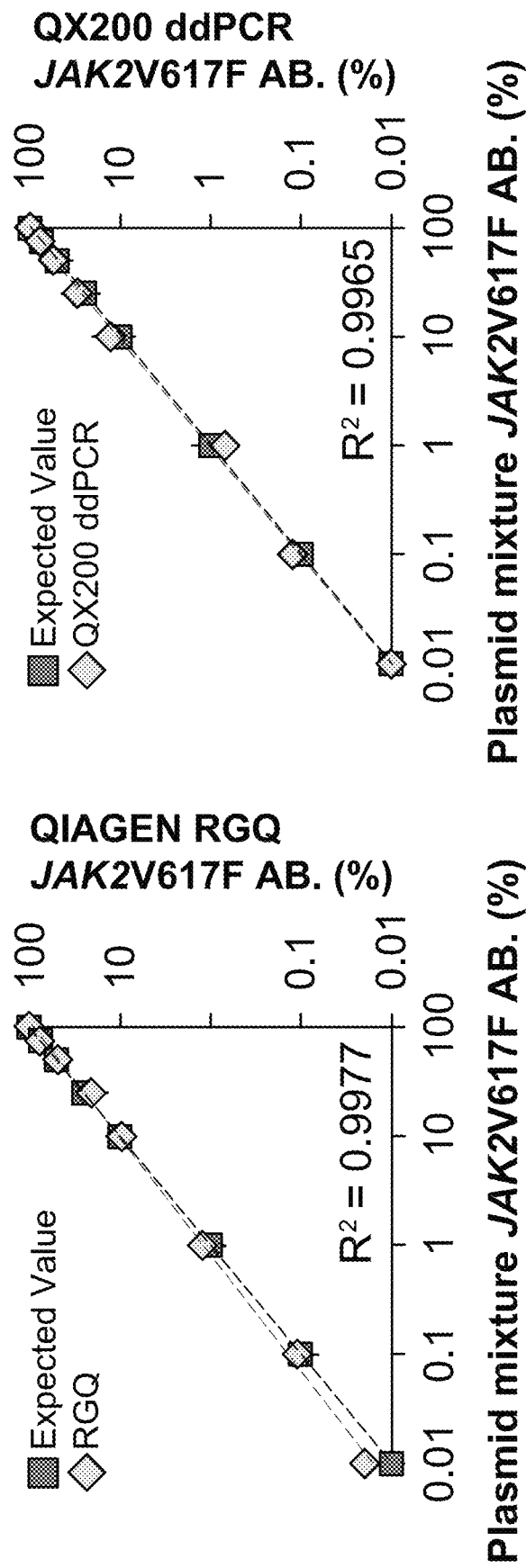
FIG. 2 shows correlation plots between expected and observed JAK2 V617F mutant allele burdens (AB) of recombinant plasmid mixtures measured by Qiagen RGQ PCR kit and Bio-Rad QX200 ddPCR kit.

Results:

FIG. 2 shows the correlation plots between the expected JAK2 V617F mutant allele burden of the recombinant plasmid mixtures and the observe one measured by Qiagen RGQ PCR kit and Bio-Rad QX200 ddPCR kit. As shown in FIG. 2, the expected JAK2 V617F mutant allele burden and the observed one determined using the Qiagen RGQ PCR kit has an excellent correlation therebetween, with calculated $R^2$ value of 0.9977. Similarly, a nearly perfect match was also found between the expected JAK2 V617F mutant allele burden and the observed one determined using the Bio-Rad QX200 ddPCR kit, with calculated $R^2$ value of 0.9965.

Taken together, these results indicate the reliability of the wild-type and mutant target recombinant plasmids of this disclosure in generating standard diluents of mutant allele for quantification of JAK2 V617F mutant allele burden.

JAK2_exon 21 ($C_{t,HEX}$). Copy number normalization was performed based on the obtained ΔCt value with the equation:

$$\Delta C_t = C_{t,FAM} - C_{t,HEX}$$

TABLE 3

| | Contents | Volume (μL) |
|---|---|---|
| | DNA template (0.1 μg/μL) | 1 |
| JAK2_exon 14 mutant allele-specific primers and probe | H_JAK2_V617_F (150 nM) | 0.5 |
| | H_JAK2_V617_R (150 nM) | 0.5 |
| | H_JAK2_probe_FAM (200 nM) | 0.5 |
| JAK2_exon 21-specific primers and probe | H_JAK2_ref_ex21_F (150 nM) | 0.5 |
| | H_JAK2_ref_ex21_R (150 nM) | 0.5 |
| | H_JAK2_ref_probe_HEX (200 nM) | 0.5 |
| | GoTaq ® Probe qPCR Master Mix RA6100 (Promega) | 10 |
| | DEPC-treated d₂H₂O. | 6.0 |

Operation conditions: Denaturation at 95° C. for 10 min, followed by 40 cycles of the following reactions: denaturation at 95° C. for 15 sec, and primer annealing and extension at 60° C. for 1 min.

TABLE 4

| | Primer/Probe | Nucleotide sequence (5'→3') | SEQ ID NO. |
|---|---|---|---|
| JAK2_exon 14 mutant allele-specific primers and probe | H_JAK2_V617_F | Ttatggacaacagtcaaacaacaattc | 8 |
| | H_JAK2_V617_R | Cttactctcgtctccacaaaa | 9 |
| | H_JAK2_probe_FAM | FAM-ttgtactttttttttccttagtctttc tttgaagcagca-IABkFQ | 10 |
| JAK2_exon 21-specific primers and probe | H_JAK2_ref_ex21_F | ggaatatttaccatatggaagtttacgagact | 11 |
| | H_JAK2_ref_ex21_R | caacacggttgcttcatctacagca | 12 |
| | H_JAK2_ref_probe_HEX | HEX-acggatagatcacataaaacttctgcag tacaca-IABkFQ | 13 |

Note:
FAM, HEX and IABkFQ respectively represent fluorescein, hexachloro-fluorescein and Iowa Black® FQ.

Example 3. Quantification of JAK2 V617F Mutant Allele Burden in the Recombinant Plasmid Mixtures and in Clinical Samples by Quantitative Duplex PCR Assay A. Creation of Standard Curves of JAK2 V617F Mutant Allele Burden 1. Plasmid-based standard curves:

Seven recombinant plasmid mixtures (respectively having JAK2 V617F mutant allele burdens of 100%, 10%, 1%, 0.1%, 0.01%, 0.01% and 0%) were prepared according to the method described in Example 2. Each of these recombinant plasmid mixtures serving as DNA templates was subjected to quantitative duplex PCR assay, which was performed on a Rotor-Gene Q (RGQ) 5plex HRM Platform (Cat No.: 9001580, Qiagen, Germany) using the PCR reaction mixture and the reaction conditions shown in Table 3. The JAK2_exon 14 mutant allele-specific primers and probe, and the JAK2_exon 21-specific primers and probe listed in Table 4 were respectively designed to quantify the amount of JAK2 V617F mutant allele through the cycle threshold value of JAK2 V617F (i.e., $C_{t,FAM}$) and the amount of JAK2_exon 21 through the cycle threshold value of To increase the specificity of JAK2 V617F detection and accurate quantification of the JAK2 V617F mutant allele burden, a refined quantitative duplex PCR assay (i.e., quantitative competitive allele-specific TaqMan duplex PCR (qCAST-Duplex PCR) assay) was conducted by further adding 0.2 μL of an oligonucleotide blocker (SEQ ID No: 14), which is a JAK2 wild-type allele-specific blocker designed with a di-deoxycytidine at its 3' end (3'-ddCTP) to inhibit the binding of the JAK2 exon 14 mutant allele-specific primers to the wild-type allele sequence of JAK2, into the q-PCR reaction mixture as shown in Table 3.

Afterwards, the thus obtained $\Delta C_t$ values of the recombinant plasmid mixtures in the presence and absence of the oligonucleotide blocker were respectively used to create the standard curves of the JAK2 V617F mutant allele burden (i.e., plasmid-based standard curves).

2. Cell-based standard curve:

In comparison with the standard curves created by the recombinant plasmid mixtures in the presence of the oligonucleotide blocker as described above, two cell lines, i.e., HEL cells and UKE-1 cells, were used to create standard curves in quantifying JAK2 V617F mutation (i.e, cell-based standard curves) using either HCK gene or JAK2 gene as the internal control. The designation of "cell-gene" is used to represent the cellular origin of DNA (i.e., HEL cells or UKE-1 cells) and the internal control gene (i.e., HCK gene or JAK2 gene) of the four cell line-based standard curves thus obtained, i.e., HEL-JAK2, HEL-HCK, UKE-1-JAK2 and UKE-1-HCK.

To be specific, genomic DNA of HEL and UKE-1 cells was extracted and purified using TRI Reagent® (Cat. No.: T9424, Sigma-Aldrich). The purified genomic DNA of the respective cell type was mixed with an appropriate amount of DNA from a healthy adult individual, so as to obtain five DNA standard diluents that have a respective one of JAK2 V617F mutant allele burdens (i.e., 100%, 50%, 10%, 1%, and 0.1%). Each of the standard diluents serving as DNA templates was subjected to the above-mentioned qCAST-Duplex PCR assay using the PCR reaction mixture and the reaction conditions shown in Table 3, in which JAK2 gene served as the internal control. When HCK gene served as the internal control, the JAK2_exon 21-specific primers and probe in Table 3 was replaced with HCK-specific primers and probe shown in Table 5, which were designed to quantify the amount of HCK amplicons $C_{t,HEX}$).

resulted with accelerated amplification of the JAK2 exon 21 DNA initiating at nearly identical cycles of the quantitative PCR reactions which were not affected by the presence of the oligonucleotide blocker.

Figure 4:
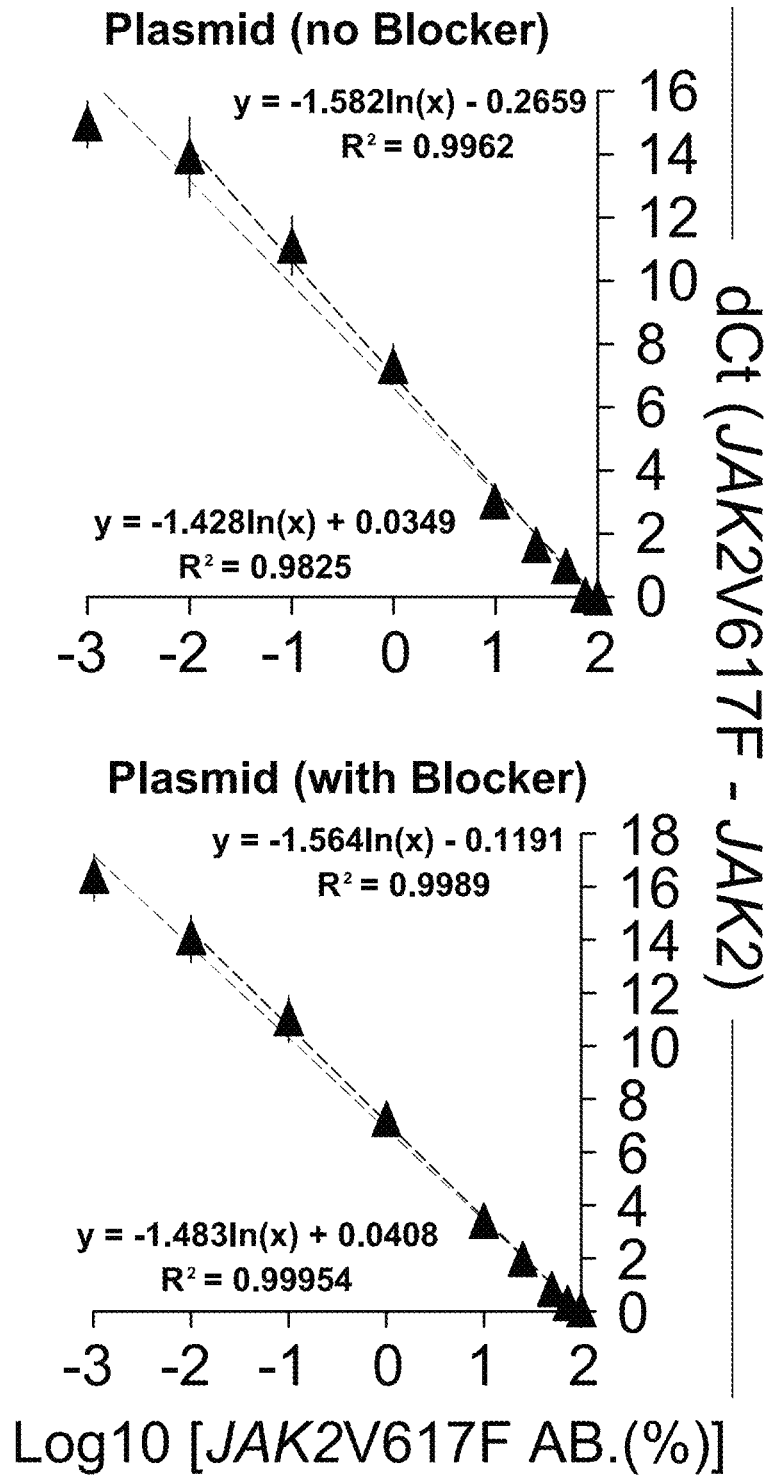
FIG. 4 shows plasmid-based standard curves created with or without (no) the oligonucleotide blocker for quantification of JAK2 V617F mutant allele burden.

As shown in FIG. 4, the standard curves of the recombinant plasmid mixtures created based on the amplification curves of JAK2 V617F mutation and JAK2 exon 21 respectively in the presence and absence of the oligonucleotide blocker achieve excellent correlation with the expected line (dashed grey). In particular, the standard curve created in the presence of the oligonucleotide blocker was more closely superimposed with the expected line (dashed grey) than the one created without the oligonucleotide blocker, especially for samples with low JAK2 V617F mutant allele burden.

The above results affirmed the unequivocal accuracy of using the plasmid mixtures to create a standard curve in quantifying JAK2 V617F mutant allele burden. In addition, by adding the oligonucleotide blocker, which impedes the binding of the JAK2 mutant allele-specific primers to the wild-type DNA template to reduce non-specific amplification, the sensitivity of the qCAST-Duplex PCR assay could be greatly improved.

TABLE 5

| Gene | Primer/Probe | Nucleotide sequence (5'→3') | SEQ ID NO. |
|---|---|---|---|
| HCK-specific primers and probe | H_HCK_F | tattagcaccatccataggaggctt | 15 |
| | H_HCK_R | gttagggaaagtggagcggaag | 16 |
| | H_HCK_probe_HEX | HEX-taacgcgtccaccaaggatgcgaa-IABkFQ | 17 |

Figure 3:
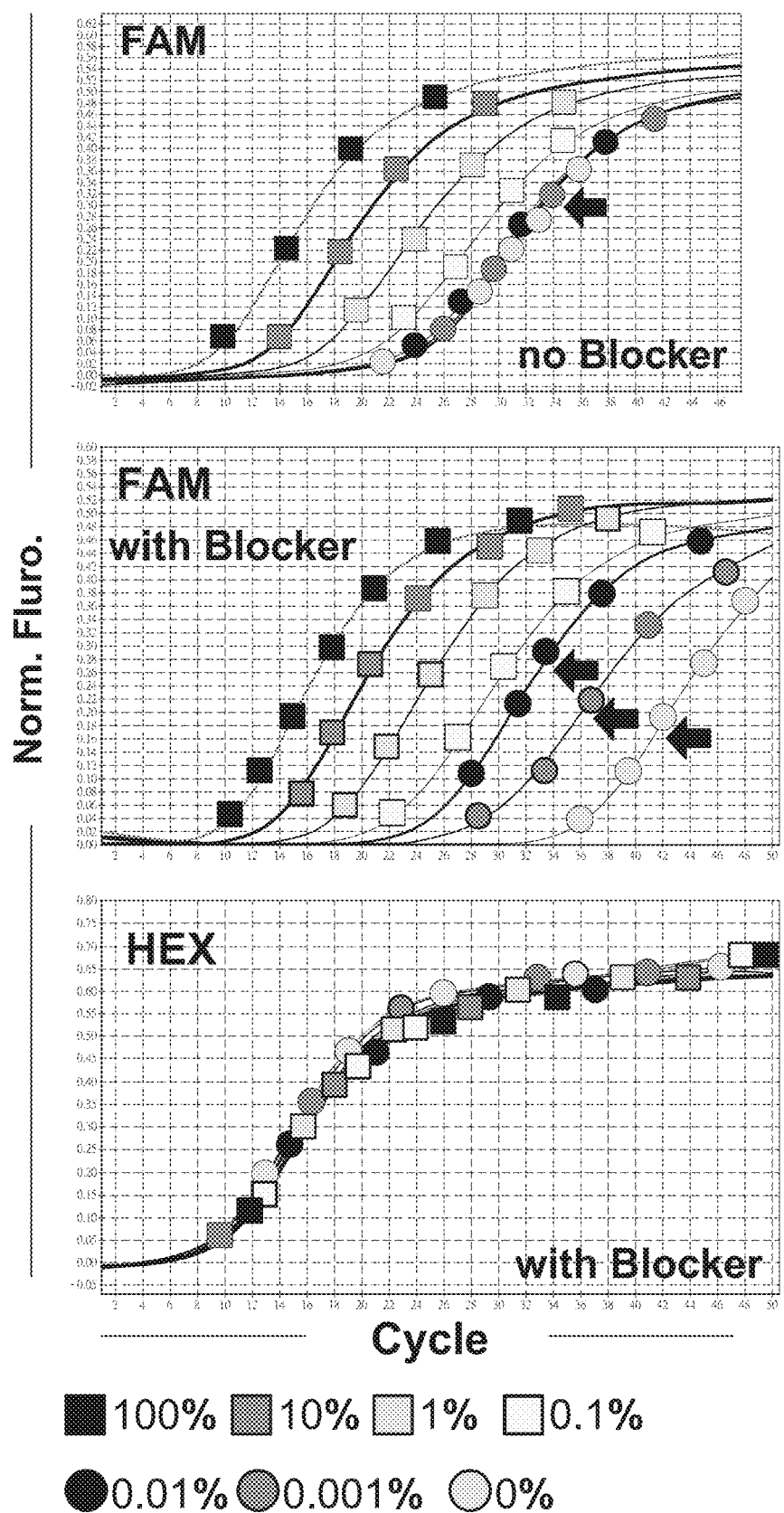
FIG. 3 shows amplification curves of recombinant plasmid mixtures having different JAK2 V617F mutant allele burdens with or without (no) an oligonucleotide blocker, in which JAK2 V617F mutation and JAK2 exon 21 are respectively detected by fluorescein (FAM)-emitting and hexachloro-fluorescein (HEX)-emitting probes.

Results:

FIG. 3 shows the amplification curves of JAK2 V617F mutation (quantified by the FAM-emitting probe) and JAK2 exon 21 (quantified by the HEX-emitting probe) in the recombinant plasmid mixtures having different JAK2 V617F mutant allele burdens, obtained in the presence or absence of the oligonucleotide blocker. FIG. 4 shows the plasmid-based standard curves obtained by calculating $\Delta C_t$ values based on the amplification curves of FIG. 3.

Figure 5:
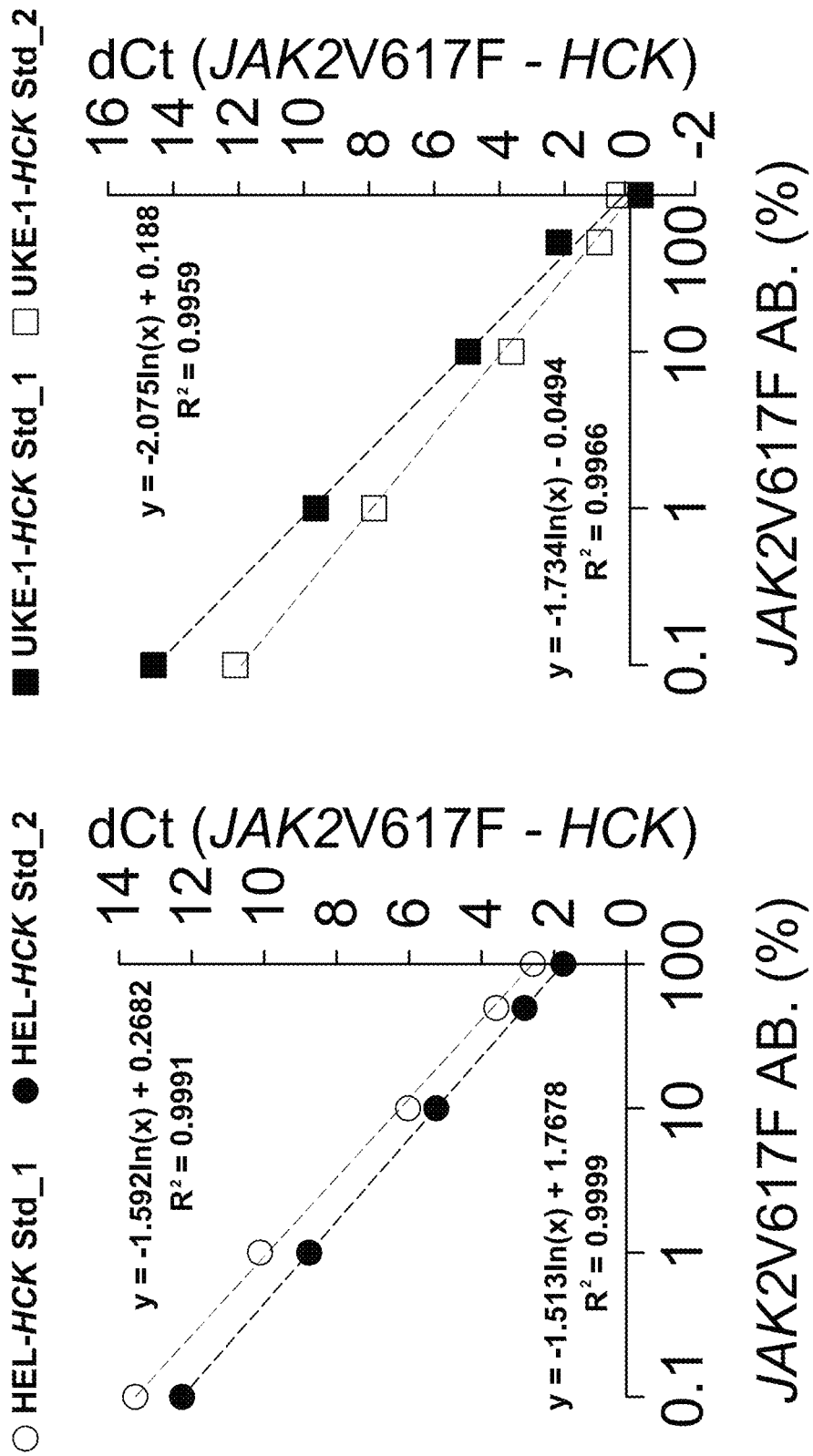
FIG. 5 shows cell-based standard curves for quantification of JAK2 V617F mutant allele burden using two different batches of cells as standard preparation, in which HEL-HCK represents the standard curve created by employing HEL cells as standards with HCK gene as an internal control, and UKE-1-HCK represents the standard curve created by employing UKE-1 cells as standards with HCK gene as an internal control.

As shown in FIG. 3, there were no discrepancy in the quantification of the JAK2 V617F mutant allele burden in the recombinant plasmid mixtures containing JAK2 V617F mutant allele burdens ranging from 100% to 0.01%, in which the $C_{t,FAM}$ values of the recombinant plasmid mixture with 0.01% JAK2 V617F mutant allele burden determined respectively in the presence and absence the oligonucleotide blocker were both 36 cycles. However, the amplification curves of the recombinant plasmid mixtures containing 0.01%, 0.001% and 0% JAK2 V617 mutant allele burdens largely overlapped with each other in the absence of the oligonucleotide blocker, and in particular, the $C_{t,FAM}$ value of the recombinant plasmid mixture containing 0.001% JAK2 V617F mutant allele burden fluctuated between 36 and 37, which was caused by non-specific amplification, resulting in difficult differentiation between the recombinant plasmid mixtures containing 0.001% and 0.01% JAK2V617F mutant allele burdens. In other words, with the addition of the oligonucleotide blocker, the amplification curves of the recombinant plasmid mixtures containing 0.01%, 0.001% and 0% JAK2 V617 mutant allele burdens were explicitly separated to improve discrimination thereamong. In addition, the considerably overlapping amplification curves as shown by the quantification of JAK2 exon 21 as internal control suggested that unequivocal q-PCR FIG. 5 shows cell-based standard curves for quantification of JAK2 V617F mutant allele burden, which were created by employing various DNA diluents from two different batches of HEL or UKE-1 cells as standards in the qCAST-Duplex PCR assay with HCK gene as the internal control. As shown in FIG. 5, there was an apparent shift between the two HEL-HCK standard curves obtained from two different batches of HEL cells, and similar results were also found in the two UKE-1-HCK standard curves. The results indicate prominent inconsistency in using genomic DNA extracted from HEL and UKE-1 cells as standards in the quantification of JAK2 V617F mutant allele burden.

B. Quantification of JAK2 V617F Mutant Allele Burden in MPN Patients with Plasmid-Based or Cell-Based Standard Curves To assess the accuracy of the standard curves obtained in section A of this example, five MPN patients, which includes four JAK2 V617F-positive patients (i.e., MPN 3, MPN 4, MPN 11 and MPN 15) and one JAK2 V617F-negative patient (i.e., MPN 34), were recruited to conduct a preliminary analysis. The DNA test sample of each MPN patient, which was prepared according to the procedures as described in the preceding section, entitled "3. Study population, blood sample collection and DNA extraction," of the General Experimental Materials, was subjected to the qCAST-Duplex PCR assay as described in section A of this example, which was performed in triplicates. The JAK2 V617F mutant allele burden of the respective patient was determined by correlating the obtained $\Delta C_t$ value with one of the plasmid-based standard curve (created in the presence of the oligonucleotide blocker) and the four cell-based standard curves created in section A of this example.

For the purpose of comparison, the JAK2 V617F mutant allele burdens of the five MPN patients were also determined using the Bio-Rad QX200 ddPCR kit as mentioned in Example 2.

Moreover, the DNA test samples from further recruited 32 MPN patients (25 having JAK2 mutation) were subjected to the same qCAST-Duplex PCR assay as described above. The JAK2V617F mutant allele burdens of each sample respectively determined based on the plasmid-based standard curve and cell-based standard curves (including HEL-HCK and UKE-1-HCK) were calculated, and were then analyzed using linear regression and Pearson's correlation analysis to determine the relationship therebetween.

Results:

Table 6 shows the JAK2 V617F mutant allele burdens in the five MPN patients determined by qCAST-Duplex PCR assay using the plasmid-based and cell-based standard curves, and by Bio-Rad QX200 ddPCR kit.

As shown in Table 6, when the plasmid-based standard curve and qCAST-Duplex PCR were used in quantifying JAK2 V617F mutant allele burden, the thus determined value in the respective sample was similar to that determined using Bio-Rad QX200 ddPCR PCR kit, and was also highly consistent with minimal variations. Furthermore, in the MPN patient deemed to be JAK2 V617F-negative (i.e., M34), the mutant allele burden thus determined was unequivocally below 0.01%, indicating use of qCAST-Duplex PCR assay and the plasmid-based standard curve can achieve a relatively lower detection limit for JAK2 V617F mutant allele burden. In contrast, when the cell-based standard curves were used along with qCAST-Duplex PCR to quantify JAK2 V617F mutant allele burden, overestimated JAK2 V617F mutant allele burdens with significant discrepancy were observed, suggesting that use of HEL or UKE-1 cells as a standard might lead to inconsistent data acquisition, and possibly false-positive results.

Taken together, these data indicate both HEL and UKE-1 cells are unreliable sources, being not useful genomic DNA standards for JAK2 V617F allele burden quantification. In contrast, reproducible and affirmative results in quantifying JAK2 V617F mutant allele burden can be obtained by virtue of the qCAST-Duplex PCR assay based on the standard curve created by the recombinant plasmids of this disclosure.

Example 4. Validation of the Accuracy of qCAST-Duplex PCR Assay Based on the Plasmid-Based Standard Curve for Quantification of JAK2 V617F Mutant Allele Burden in MPN Patients Experimental Procedures:

To assess the sensitivity (detection limit) of the qCAST-Duplex PCR assay using the plasmid-based standard curve created in section A of Example 3, a random set of DNA mixtures from JAK2-mutated MPN patients were serially diluted with healthy adult individuals' DNA, so as to obtain 8 DNA test samples (i.e., S1, S2, S3, S4, S5, S6, S7 and S8) respectively with low JAK2V617F mutant allele burdens (i.e., 2%, 1%, 0.2%, 0.1%, 0.02%, 0.01%, 0.002%, and 0.001%). Each of the 8 DNA test samples was run in triplicates with the qCAST-Duplex PCR assay, and in duplicates with the Qiagen RGQ PCR kit.

In addition, 70 MPN patients (including 55 JAK2 V671-positive and 15 JAK2 V671-negative MPN patients) and 30 healthy adult individuals were enrolled for comprehensive analysis. The DNA test samples from those subjects were subjected to four commonly used sensitive assays, including

TABLE 6

| | JAK2 V617F mutant allele burden (%) | | | | | |
|---|---|---|---|---|---|---|
| | | qCAST-Duplex PCR | | | | |
| MPN | Plasmid-based | Cell-based standard curve | | | | Bio-Rad QX200 |
| patients | standard curve | HEL-HCK | UKE-1-HCK | HEL-JAK2 | UKE-1-JAK2 | ddPCR |
| M03 | 45.324 ± 0.025 | 171.513 ± 87.172 | 57.748 ± 21.265 | 24.151 ± 2.852 | 50.154 ± 7.47 | 43.712 ± 0.413 |
| M04 | 72.781 ± 0.035 | 516.545 ± 16.224 | 121.462 ± 37.481 | 72.906 ± 1.513 | 89.703 ± 18.733 | 75.401 ± 0.700 |
| M11 | 0.085 | 0.212 ± 0.076 | 0.232 ± 0.080 | 0.032 ± 0.002 | 0.051 ± 0.0471 | 0.070 |
| M15 | 92.219 ± 0.041 | 634.357 ± 4.241 | 123.569 ± 37.514 | 111.335 ± 26.401 | 98.221 ± 12.422 | 97.122 ± 0.901 |
| M34 | 0.004 | 0.135 ± 0.035 | 0.028 ± 0.001 | 0.005 ± 0.006 | 0.011 ± 0.011 | 0.004 |

Note:
Expression of data as a mean value only (i.e., without the "±" sign) indicates that the standard deviation is less than 0.001.

Figure 6:
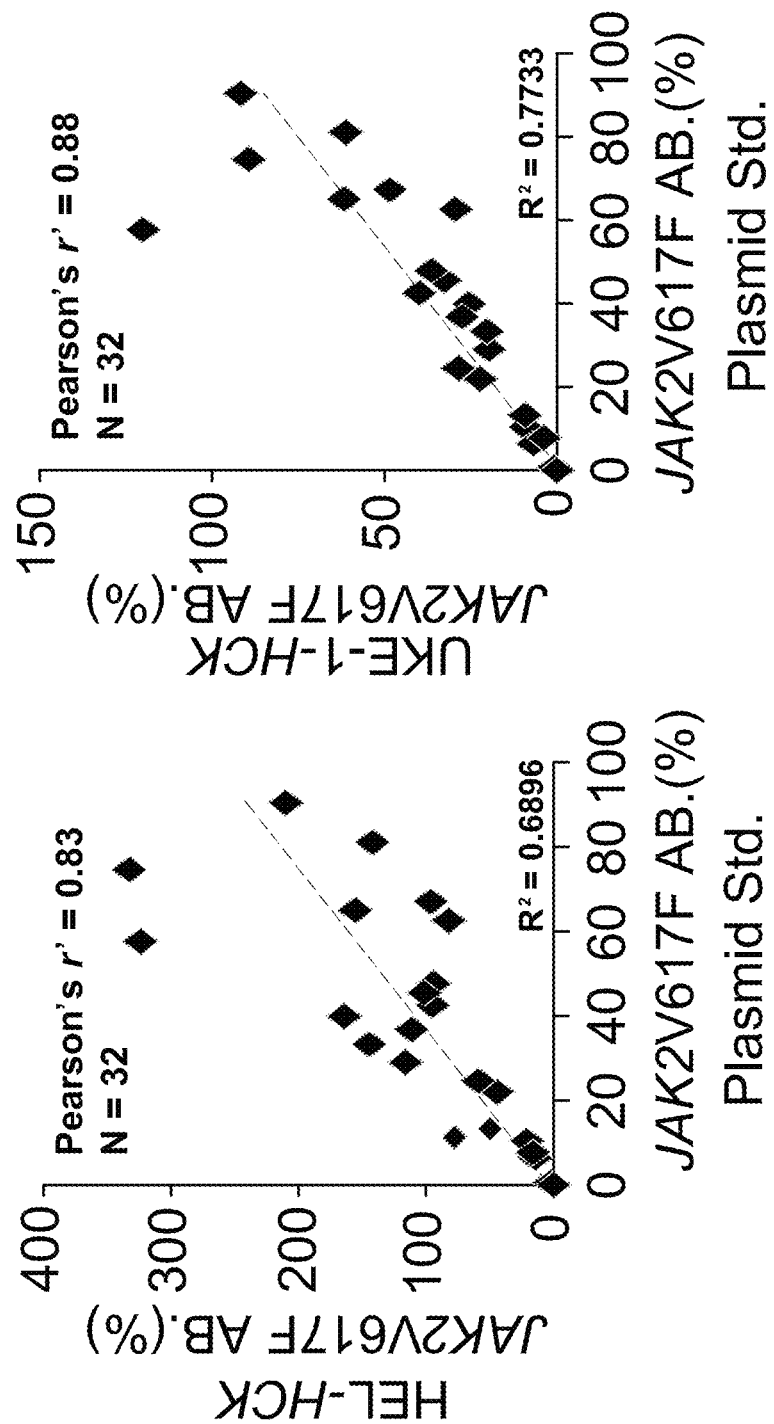
FIG. 6 shows correlation plots between the JAK2 V617F mutant allele burdens in 32 MPN patients determined based on the plasmid-based standard curve and those determined based on the cell-based standard curves HEL-HCK and UKE-1-HCK.

FIG. 6 shows correlation plots of the JAK2 V617F mutant allele burdens in 32 MPN patients determined using qCAST-Duplex PCR assays based on the plasmid-based and cell-based standard curves (i.e., HEL-HCK and UKE-1-HCK). As shown in FIG. 6, there was an apparent overestimation of JAK2 V617F mutant allele burden when HEL-HCK was used as a standard, and the plotted curves between the results obtained from the HEL-HCK standard curve and the plasmid-based standard curve demonstrated relatively poor correlation. On the other hand, the results obtained from UKE-1-HCK and the plasmid-based standard curve demonstrated slightly better correlation, but there were still quite a few outliers.

Qiagen RGQ PCR kit, Bio-Rad QX200 ddPCR kit, competitive allele-specific TaqMan (CAST) PCR kit (Applied Biosystems (ABI), MA, USA) and multiplex PCR amplicon sequencing (detailed procedures are described below), and were also subjected to qCAST-Duplex PCR assay using the plasmid-based standard curve as described in section B of Example 3, so as to determine JAK2 V617F mutant allele burdens thereof. The results obtained by qCAST-Duplex PCR assay using the plasmid-based standard curve and those obtained by the commonly used sensitive assays were compared and analysed using linear regression and Pearson's correlation analysis, so as to assess the relationship therebetween.

For the multiplex PCR amplicon sequencing, exon sequences of 35 target genes (including JAK2) of Genome Reference Consortium Human Build 37 (GRCh37/hg19) were downloaded from University of California Santa Cruz (UCSC) Genome Browser. Each of the primers designed for the target genes contained a respective adaptor, and the expected maximal PCR product size was set at less than 300 bps. A micro-fluid-based method using Access Array™ system (Fluidigm, Calif., USA) was employed to construct the sequence library for each DNA samples, and paired-end 150 bps cycle high-throughput sequencing was performed using HiSeq 2500 system (Illumina, CA, USA). After data processing, mapping and variant calling were conducted using CLC Genomics Workbench (Qiagen, Germany). Identification of JAK2 V617F mutation was based on the criteria of more than 50 coverages and an allelic frequency of more than 1%.

Figure 7:
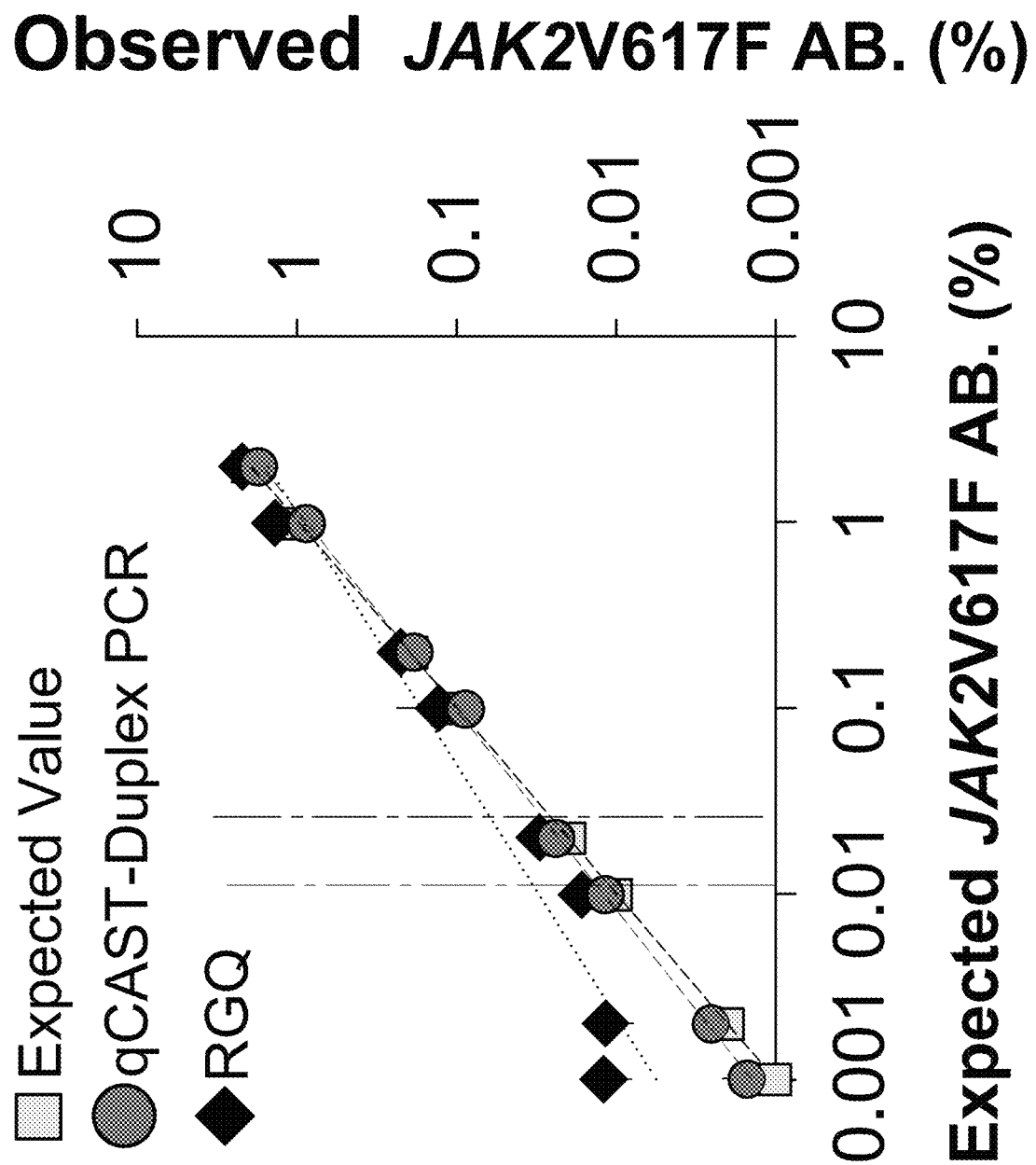
FIG. 7 shows JAK2 V617F mutant allele burdens determined by qCAST-Duplex PCR assay based on the plasmid-based standard curve and by Qiagen RGQ PCR kit in comparison with expected values thereof, in which the black and grey dash lines indicated the sensitivity (i.e., possible detection limit) of the Qiagen RGQ PCR kit and the qCAST-Duplex PCR assay.

Results:

FIG. 7 shows the JAK2 V617F mutant allele burdens for DNA test samples S1 to S8 determined by qCAST-Duplex PCR assay using the plasmid-based standard curve, and determined by Qiagen RGQ PCR kit. As shown in FIG. 7, the JAK2 V617F mutant allele burdens in DNA test samples S1 to S8 quantified by the qCAST-Duplex PCR assay have higher similarity and excellent correlation to the expected values, even in the DNA test samples with a very low mutant allele burden (≤0.01%). In contrast, when using Qiagen RGQ PCR kit, overestimation of the JAK2 V617F mutant allele burdens was observed in the DNA test samples having an expected mutant allele burden below 0.01%. This result indicates that qCAST-Duplex PCR assay based on the plasmid-based standard curve of this disclosure yields highly accurate and reproducible results in quantifying JAK2 V617F mutant allele burden, even for a value below 0.01%.

Table 7 shows the JAK2 V617F mutant allele burdens in the MPN patients and healthy adult individuals determined by the qCAST-Duplex PCR of this disclosure and the four commonly used sensitive assays.

Figure 8:
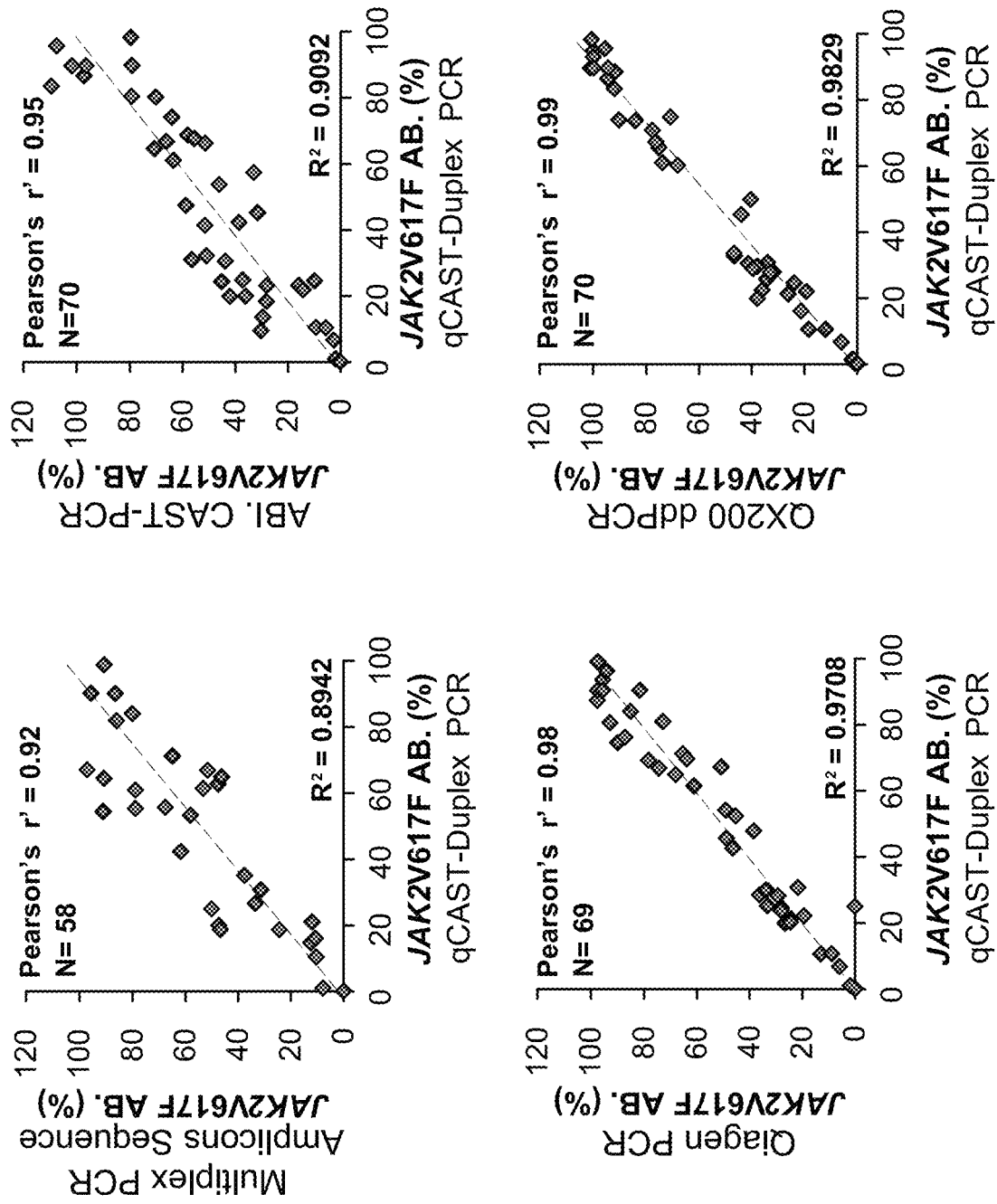
FIG. 8 shows correlation plots between the JAK2 V617F mutant allele burden in MPN patients and healthy adult individuals determined by qCAST-Duplex PCR assay based on the plasmid-based standard curve and those determined by any one of multiplex PCR amplicon sequencing, ABI CAST PCR kit, Qiagen RGQ PCR kit and Bio-Rad QX200 ddPCR kit.

FIG. 8 shows correlation plots between the JAK2 V617F mutant allele burdens determined by the qCAST-Duplex PCR assay based on the plasmid-based standard curve and those determined by other assay.

As shown in Table 7 and FIG. 8, quantification results of JAK2 V617F mutant allele burdens measured by the qCAST-Duplex PCR assay based on the plasmid-based standard curve of this disclosure show good correlation and are consistent with those obtained by any one of the four commonly used sensitive assays, and none of the healthy adult individuals was tested JAK2V617F-positive in any of the assessments, suggesting that the performance of the method of this disclosure is comparable and accurate with low false positive rate. In particular, the results are especially consistent between measurements using the qCAST-Duplex PCR with the plasmid-based standard and the Bio-Rad QX200 ddPCR assay, which is widely considered as one of the most reliable assay to quantify JAK2 mutant allele burden, but might be not easily affordable in clinical settings. Therefore, the quantification method of this disclosure using the qCAST-Duplex PCR assay and the recombinant plasmids as standards has an advantage of being more cost-effective.

In conclusion, by employing the qCAST-Duplex PCR assay and use of the recombinant plasmids as standards, the method of this disclosure can yield reproducible and affirmative results for the quantification of JAK2 V617F mutant allele burden, thereby improving the accuracy in molecular diagnostics of MPN.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

TABLE 7

| Test subjects (total number), test result (number of test subjects), or JAK2V617F allele burden (%) (number of test subjects) | qCAST-Duplex PCR | Bio-Rad QX200 ddPCR | Qiagen RGQ PCR | ABI CAST PCR | Multiplex PCR amplicon sequencing |
|---|---|---|---|---|---|
| MPN patients | 70 | 70 | 69 | 70 | 58 |
| JAK2V617F (+) | 55 | (55/55) | (49/55) | (50/55) | (32/36) |
| >50% | 23 | (23/23) | (22/22) | (23/23) | (17/18) |
| 10-50% | 20 | (20/20) | (20/20) | (19/20) | (13/13) |
| 1-10% | 4 | (4/4) | (4/4) | (5/4) | (1/1) |
| 0.1-1% | 1 | (2/1) | (1/2) | (2/1) | (0/1) |
| 0.01-0.1% | 7 | (6/7) | (2/7) | (1/7) | (0/3) |
| JAK2V617F(−) | 15 | (15/15) | (21/15) | (20/15) | (26/22) |
| Healthy adults | 30 | 8 | 4 | 25 | n.d. |
| >0.1% | 0 | 0 | 0 | 0 | n.d. |
| >0.01% | 0 | 0 | 0 | 0 | n.d. |
| None | 30 | 4 | 4 | 25 | n.d. |

Note:
1) The number in the parentheses denotes detected case number/expected case number. With limited availability in some of the assays, the number of DNA samples analyzed differs between the assays.
2) "n.d." indicates no detection.

What is claimed is:

1. A method of quantifying a mutant allele burden of a non-fusion target gene in a subject, comprising:
    providing a first plasmid that includes a mutant allele sequence located within a first exon of the non-fusion target gene, and an internal control sequence within and corresponding to at least part of a second exon of the non-fusion target gene, the second exon being different from the first exon;
    providing a second plasmid that includes a wild-type allele sequence located within the first exon of the non-fusion target gene, and the internal control sequence;
    subjecting genomic DNA of the subject to a first quantitative polymerase chain reaction using a reaction mixture containing a mutant allele-specific primer pair and a first detectable probe for detecting the mutant allele sequence, and an internal control sequence-specific primer pair and a second detectable probe for detecting the internal control sequence, so as to measure a mutant allele expression level of the non-fusion target gene;
    subjecting standard diluents of the first plasmid formed from serial dilution with the second plasmid to a second quantitative polymerase chain reaction using the reaction mixture, so as to create a standard curve of the mutant allele burden of the non-fusion target gene; and
    correlating the measured mutant allele expression level of the non-fusion target gene to the standard curve, so as to determine the mutant allele burden of the non-fusion target gene in the subject,
    wherein the reaction mixture for each of the first and second quantitative polymerase chain reaction further includes a blocking agent that hybridizes to the wild-type allele sequence of the non-fusion target gene and that inhibits binding of at least one primer of the mutant allele-specific primer pair to the wild-type allele sequence of the non-fusion target gene.

2. The method as claimed in claim 1, wherein the mutant allele sequence has a nucleotide length that is substantially identical to that of the wild-type allele sequence, and the first plasmid has a nucleotide length that is substantially identical to that of the second plasmid.

3. The method as claimed in claim 1, wherein the blocking agent is an oligonucleotide having a non-extendable moiety at 3'-terminus, the non-extendable moiety being selected from the group consisting of peptide nucleic acid, locked nucleic acid, zip nucleic acid, bridged nucleic acid, threose nucleic acid, triazole nucleic acid, amino-C7, non-extendable nucleotide, minor groove binder, and combinations thereof.

4. The method as claimed in claim 3, wherein the blocking agent is an oligonucleotide having di-deoxynucleotide triphosphates at the 3' terminus thereof.

5. The method as claimed in claim 1, wherein the non-fusion target gene is a disease-associated gene.

6. The method as claimed in claim 5, wherein the disease-associated gene is selected from the group consisting of cancer-associated genes, genes associated with a hereditary disease, and combinations thereof.

7. The method as claimed in claim 6, wherein the non-fusion target gene is selected from the group consisting of JAK2, K-Ras, B-Raf, EGFR, and combinations thereof.

8. The method as claimed in claim 7, wherein the non-fusion target gene is JAK2.

9. The method as claimed in claim 8, wherein the mutant allele sequence is JAK2 V617F.

10. The method as claimed in claim 8, wherein the second exon is exon 21 of JAK2.

* * * * *